United States Patent
Hauger et al.

(10) Patent No.: US 9,727,962 B2
(45) Date of Patent: Aug. 8, 2017

(54) SYSTEM FOR VISUALIZING TISSUE IN A SURGICAL REGION

(71) Applicant: Carl Zeiss Meditec AG, Jena (DE)

(72) Inventors: Christoph Hauger, Aalen (DE); Roland Guckler, Aalen-Dewangen (DE); Helge Jess, Oberkochen (DE); Joachim Steffen, Westhausen (DE); Werner Nahm, Buehlerzell (DE)

(73) Assignee: Carl Zeiss Meditec AG, Jena (DE)

( * ) Notice: Subject to any disclaimer, the term of this patent is extended or adjusted under 35 U.S.C. 154(b) by 537 days.

(21) Appl. No.: 13/946,716

(22) Filed: Jul. 19, 2013

(65) Prior Publication Data
US 2013/0307953 A1 Nov. 21, 2013

Related U.S. Application Data

(63) Continuation of application No. PCT/EP2011/072651, filed on Dec. 13, 2011.

(30) Foreign Application Priority Data

Jan. 21, 2011 (DE) .................... 10 2011 002 990

(51) Int. Cl.
*G06T 7/00* (2017.01)
*A61B 5/00* (2006.01)
*G01N 21/64* (2006.01)

(52) U.S. Cl.
CPC .......... *G06T 7/0012* (2013.01); *A61B 5/0071* (2013.01); *G01N 21/6458* (2013.01); *G01N 2021/6417* (2013.01)

(58) Field of Classification Search
CPC ......... A61B 19/52; A61B 5/06; A61B 5/0059; G01N 21/6458; G01N 21/6456; G06T 7/0012; G02B 23/26; H04N 2005/2255
See application file for complete search history.

(56) References Cited

U.S. PATENT DOCUMENTS 6,537,211 B1   3/2003 Wang et al.
7,235,045 B2   6/2007 Wang et al.
(Continued)

FOREIGN PATENT DOCUMENTS

WO   WO 2004/005895 A1   1/2004

OTHER PUBLICATIONS

International Preliminary Report on Patentability dated Aug. 1, 2013 of international application PCT/EP2011/072651 on which this application is based.
(Continued)

*Primary Examiner* — Obafemi Sosanya
(74) *Attorney, Agent, or Firm* — Walter Ottesen, P.A.

(57) ABSTRACT

The invention relates to a system for visualizing characteristic tissue with a colorant in a surgical region. The system contains a detection unit which detects light from at least one object point in the surgical region. The system has a computer unit which is connected to the detection unit and drives a visualization unit which displays an image of an area in the surgical region. The computer unit determines the color coordinate in a color space with respect to the light from a point from the object point in the surgical region. Depending on the position of the color coordinate determined with respect to the object point, the computer unit calculates a color coordinate information ("0", "1") for controlling the visualization unit by comparing information concerning the determined color coordinate of the object point with information concerning a characteristic reference color coordinate.

18 Claims, 9 Drawing Sheets

(56) References Cited

U.S. PATENT DOCUMENTS

| | | | |
|---|---|---|---|
| 2001/0056237 A1* | 12/2001 | Cane | A61B 5/0059 600/475 |
| 2007/0137908 A1* | 6/2007 | Fujiwara | B60K 6/26 180/65.22 |
| 2008/0049314 A1* | 2/2008 | Steffen | G02B 6/4298 359/389 |
| 2009/0137908 A1* | 5/2009 | Patwardhan | A61B 5/0059 600/476 |
| 2009/0202119 A1* | 8/2009 | Hefti | A61B 5/0059 382/128 |
| 2011/0044910 A1* | 2/2011 | Lin | A61B 5/0059 424/9.6 |

OTHER PUBLICATIONS

International Search Report dated Mar. 30, 2012 of international application PCT/EP2011/072651 on which this application is based.

* cited by examiner

SYSTEM FOR VISUALIZING TISSUE IN A SURGICAL REGION

CROSS REFERENCE TO RELATED APPLICATIONS

This application is a continuation application of international patent application PCT/EP2011/072651, filed Dec. 13, 2011, designating the United States and claiming priority from German application 10 2011 002 990.7, filed Jan. 21, 2011, and the entire content of both applications is incorporated herein by reference.

FIELD OF THE INVENTION

The invention relates to a system for visualizing characteristic tissue in a surgical region, having a detection unit capturing light from at least one object point, having a computer unit connected to the detection unit and having a visualization apparatus actuated by the computer unit and displaying an image of an area in the surgical region.

BACKGROUND OF THE INVENTION

Such a system is described in United States patent application publication 2009/0202119. This system comprises a surgical microscope, which is designed for observing the surgical region using fluorescence light. The surgical microscope comprises an illumination apparatus with a xenon lamp as light source. There is a narrowband filter in the illumination apparatus. This filter is transmissive for light in the wavelength region between 390 nm and 410 nm. Using light of this wavelength, it is possible to excite the dye protoporphyrin IX (PPIX) to fluoresce. The dye PPIX can be selectively accumulated in pathologically changed tumor-diseased cells. The surgical microscope comprises a detection apparatus, which contains a color camera. This color camera can be used to capture the fluorescence light from PPIX. The color camera is connected to a computer unit for image processing. In this computer unit, the signal from the color camera corresponding to the red color channel is converted into a grayscale-value image. Subsequently, the intensity of each pixel in the grayscale-value image is compared to a threshold. Boundary intensity lines are then calculated from this comparison. These boundary intensity lines are displayed together with the surgical area on a visualization apparatus having a screen. The boundary intensity lines surround tumor-diseased tissue. As a result, the boundary intensity lines make it easier for an operator to identify tumor tissue in a surgical region.

Experience has shown that the system described in United States patent application publication 2009/0202119 cannot always reliably visualize the position of the edge regions of tissue afflicted by tumor using the boundary intensity lines.

"R. Ishihara et al., Quantitative Spectroscopic Analysis of 5-ALA-induced Protoporphyrin IX Fluorescence Intensity in Diffusely Infiltrating Astrocytomas, Neuro Med Chir (Tokyo) 47, 53 (2007)" has disclosed that it is possible to distinguish healthy regions from regions afflicted by tumor in tissue, enriched with the substance PPIX, of the human brain by evaluating intensity peaks which occur at characteristic wavelengths in the fluorescence spectrum of protoporphyrin IX. This method requires a high degree of measurement and computational complexity.

SUMMARY OF THE INVENTION

It is an object of the invention to provide a visualization system which enables an observer to distinguish pathologically different body tissue accurately and reliably in a surgical region.

This object is achieved by a system of the type mentioned at the outset, for visualizing tissue, in which the computer unit, for the purposes of controlling the visualization apparatus, establishes the color coordinate in a color space for the light from the at least one object point in the surgical region and, depending on the position of the color coordinate established for the object point, calculates color coordinate information for controlling the visualization apparatus by comparing information relating to the color coordinate established for the object point with the information relating to a characteristic reference color coordinate.

A color coordinate in a color space within the meaning of the present invention should be understood to mean the ROB color space, set by the definition CIE 1931 by the Commission Internationale de l'Éclairage, or a further color space equivalent thereto, which can be converted into the RGB color space by a preferably reversible transformation without loss of information or with only little loss of information.

Within the meaning of the invention, a color coordinate in a color space is moreover the location defined by a number tuple (x, y) in the CIE xyY color space set by the definition CIE 1931 by the Commission Internationale de l'Éclairage. This color space is described in the article by Charles Poynton "A Guided Tour of Color Space", in New Foundations for Video Technology, Proceedings of the SMPTE Advanced Television and Electronic Image Conference, San Francisco, February 1995, pages 167 to 180. There, the CIE xyY color space is referred to as CIE chromaticity color space. The definition of this color space is specified on page 6 and page 7 of the aforementioned publication. A color coordinate in the CIE xyY color space is independent of the luminance or intensity of the light underlying the color coordinate. Moreover, within the meaning of the present invention, a color space is any color space into which the CIE xyY color space can be converted by a reversible transformation without loss of information and therefore has the same information content as the CIE xyY color space. By way of example, such a color space is the L*a*b* color space CIE 1976 defined in part 3 of DIN 5033, the L*u*v* color space CIE 1976 defined therein or else a region in the RGB color space with color coordinates based on light from object points whose luminance or intensity is the same. Moreover, a color space within the meaning of the present invention having the same information content as the CIE xyY color space is also the XYZ color space, the $LCH_{ab}$ color space and the $LCH_{uv}$ color space, which, for example, are specified on the website www.brucelindbloom.com and which, by using a computational prescription deposited there, can be converted into one another and, in particular, into the CIE xyY color space.

The invention is moreover based on the discovery that, as a result of systematic evaluation of object point color information, the edge region of tumor tissue in the human brain, in which tumor cells have infiltrated healthy tissue, can be clearly distinguished from the remaining tissue of the tumor and from healthy tissue. The discovery of the invention is, in particular, that a reliable distinction of tumor tissue in a surgical region is possible if the tissue in the surgical region, as described above, has been marked with the dye PPIX and is excited to fluoresce by illumination with blue light in the wavelength range between 390 nm and 410 nm.

It was found that, in particular, the evaluation of object point color information, which is invariant with respect to the luminance or brightness of the light from an object point, over the whole duration of a surgical intervention in the brain of a patient enables an accurate distinction to be made between healthy tissue, tumor tissue and tissue in the edge regions of the tumor.

In the following Tables 1 and 2, the color coordinate in the CIE xyY color space and in the CIE RGB color space is specified for the light from object points. These object points respectively lie in a surgical region afflicted by a tumor. The object points are in part from different patients. The medicament Gliolan was administered orally to the patients pre-surgery. This medicament contains the substance 5ALA. Taking this medicament brings about an accumulation of the dye PPIX in tumor-diseased tissue. Under illumination with light having a wavelength of λ=400 nm, this dye fluoresces in the red spectral range. In the case of this type of illumination, healthy tissue in the human brain appears to have a blue color to an observer. The edge region of a tumor, in which there are tumor cells which have infiltrated healthy tissue, appears salmon in this case.

TABLE 1

| Location in the surgical region, consecutive number | Tissue type | Color coordinate in the CIE xyY color space | | |
|---|---|---|---|---|
| | | x | y | Y |
| 1 | Healthy | 0.19 | 0.08 | 7.7 |
| 2 | Healthy | 0.19 | 0.12 | 4.59 |
| 3 | Healthy | 0.17 | 0.09 | 1.37 |
| 4 | Healthy | 0.20 | 0.10 | 5.22 |
| 5 | Healthy | 0.19 | 0.09 | 8.08 |
| | Mean: | 0.19 | 0.09 | |
| | Standard deviation: | 0.01 | 0.01 | |
| 6 | Tumor | 0.36 | 0.18 | 5.08 |
| 7 | Tumor | 0.40 | 0.20 | 18.59 |
| 8 | Tumor | 0.34 | 0.17 | 15.84 |
| 9 | Tumor | 0.32 | 0.15 | 8.04 |
| 10 | Tumor | 0.41 | 0.21 | 7.14 |
| 11 | Tumor | 0.32 | 0.15 | 9.5 |
| 12 | Tumor | 0.39 | 0.20 | 19.19 |
| 13 | Tumor | 0.45 | 0.23 | 20.19 |
| 14 | Tumor | 0.38 | 0.19 | 8.5 |
| 15 | Tumor | 0.40 | 0.20 | 15.44 |
| 16 | Tumor | 0.40 | 0.20 | 15.14 |
| | Mean: | 0.38 | 0.19 | |
| | Standard deviation | 0.04 | 0.02 | |
| 17 | Edge region | 0.27 | 0.13 | 2.37 |
| 18 | Edge region | 0.23 | 0.10 | 3.18 |
| 19 | Edge region | 0.21 | 0.10 | 3.97 |
| | Mean: | 0.24 | 0.11 | |

TABLE 2

| Location in the surgical region, consecutive number | Tissue type | Color coordinate in the CIE RGB color space | | | | |
|---|---|---|---|---|---|---|
| | | Lum | R | G | B | R/B |
| 1 | Healthy | 57 | 93 | 17 | 219 | 0.42 |
| 2 | Healthy | 61 | 56 | 47 | 146 | 0.38 |
| 3 | Healthy | 33 | 29 | 21 | 99 | 0.89 |
| 4 | Healthy | 57 | 82 | 26 | 170 | 0.48 |
| 5 | Healthy | 67 | 97 | 25 | 217 | 0.45 |
| | Mean: | | | | | 0.40 |
| | Standard deviation: | | | | | 0.07 |
| 6 | Tumor | 59 | 116 | 18 | 182 | 1.14 |
| 7 | Tumor | 95 | 217 | 18 | 167 | 1.30 |
| 8 | Tumor | 89 | 193 | 21 | 185 | 1.04 |
| 9 | Tumor | 63 | 139 | 15 | 145 | 0.96 |
| 10 | Tumor | 63 | 141 | 15 | 163 | 1.37 |
| 11 | Tumor | 71 | 150 | 15 | 157 | 0.96 |
| 12 | Tumor | 94 | 220 | 17 | 171 | 1.29 |
| 13 | Tumor | 95 | 231 | 19 | 146 | 1.58 |
| 14 | Tumor | 71 | 150 | 18 | 122 | 1.23 |
| 15 | Tumor | 90 | 199 | 23 | 150 | 1.33 |
| 16 | Tumor | 86 | 198 | 20 | 148 | 1.34 |
| | Mean: | | | | | 1.23 |
| | Standard deviation: | | | | | 0.19 |
| 17 | Edge region | 35 | 75 | 6 | 97 | 0.77 |
| 18 | Edge region | 44 | 77 | 9 | 127 | 0.60 |
| 19 | Edge region | 49 | 79 | 16 | 147 | 0.54 |
| | Mean: | | | | | 0.64 |
| | Standard deviation: | | | | | 0.12 |

The basic concept of the invention makes use of this discovery. It consists of capturing color information, which is independent of the intensity or luminance, contained in the spectral intensity distribution of the light from an object point in order then to localize precisely the edge region of a tumor by means of this color information. To this end, depending on the position of the color coordinate established for the object point, the computer unit calculates color information in a color space, which is preferably independent of the luminance or intensity, for controlling the visualization device. The computer unit determines this color information by comparing information relating to the color coordinate established for the object point with the information relating to a characteristic reference color coordinate.

By way of example, to this end the computer unit calculates the coordinates of the color coordinate in a workspace, for example the CIE xyY color space or the L*a*b* color space CIE 1976, from the signal from image sensors in the detection unit for light from the at least one object point recorded, for example, in the RGB color space. Here, the signal from the image sensors is available in the form of coordinates in a workspace. By way of example, this color space can be the video color space Y*u*v*, which is widely used in video technology. The coordinates of the color coordinate in the workspace are items of information relating to the color coordinate established for an object point. From this, the computer unit determines color coordinate information ("0", "1"), by means of which the visualization device is controlled. By way of example, the computer unit can calculate the color information ("0", "1") from a distance norm relating to the color distance of the color between the color coordinate (x, y) established for the object point and a characteristic reference color coordinate with the coordinates ($x_c$, $y_c$). Here, the coordinates ($x_c$, $y_c$) are the information relating to the characteristic reference color coordinate.

As an alternative to this, the computer unit can also establish the coordinates of the color coordinate (R, G, B) in the RGB color space for the light from the at least one object point and calculate the color coordinate information ("0", "1") from a deviation of the ratio R/B established for the coordinates of the color coordinate (R, G, B) from the ratio $R_c/B_c$ of a characteristic reference color coordinate ($R_c$, $G_c$, $B_c$). Here, the ratio R/B then is the information of the color coordinate relating to an object point and the ratio $R_c/B_c$ is the information relating to a characteristic reference color coordinate. The reference color coordinate for healthy tissue, for diseased, tumor-afflicted tissue and for the edge region of tumor-afflicted tissue is preferably stored in a data storage medium of the computer unit.

It is advantageous if an entry unit for entering the characteristic reference color coordinate is provided in the system. This measure allows an operator to be able to establish, for different tissue types in a surgical region, the color coordinate for a characteristic reference color corresponding to the experience of the operator.

The system can contain a detection unit for capturing the color coordinate of the light from the at least one object point using a spectrometer for the spectral decomposition of light. However, it is also possible to provide in the detection unit a digital color camera, more particularly a video camera, which is sensitive to the colors red (R), green (G) and blue (B). Moreover, it is possible to design the system with an illumination unit for time-sequential RGB illumination. Then it is possible to use a light-sensitive contiguous electronic black/white image sensor, that is, an image sensor which can only capture the intensity of light but not the color thereof, as detection unit for capturing the color coordinate of the light from the at least one object point.

The system can comprise an illumination unit which provides illumination light in a wavelength range which renders it possible to excite a dye in the surgical region to fluoresce. The wavelength range of the illumination light preferably enables fluorescence to be excited in the dye PPIX and/or sodium fluorescein and/or hypericin.

The resulting spectral transmission of the optical elements in the illumination unit and the detection unit, which comprise an observation filter, is expediently selected here so that practically no light with a wavelength λ from the light used to excite the fluorescence is captured by the detection unit. By contrast, light with a wavelength λ from the wavelength range in which the fluorescence occurs enters the detection unit. It is advantageous if the spectral transmission of the optical elements of the illumination unit and the detection unit with the observation filter is configured in such a way that the illuminated tissue region can be illuminated with high intensity using light having a wavelength lying neither in the range of the excitation spectrum nor in the range of the fluorescence spectrum of a suitable dye. This is because this allows an observer to perceive the details of the illuminated tissue region independently of the fluorescence radiation as a result of the light reflected directly in this wavelength range.

It is advantageous if the illumination unit generates light in the wavelength range from at least 380 nm to 680 nm. It is expedient if the light generated by the illumination unit in this wavelength range is incoherent. The light from the surgical region captured by the detection unit is then passed through an appropriate observation filter. Here, the resultant spectral transmission of the optical elements of the illumination unit is matched to the fluorescence excitation spectrum of the dye. In particular, it is advantageous if the degree of spectral transmission of the resultant spectral transmission of the overall system consisting of the illumination unit and the observation filter is more than 5% only in a wavelength range extending over at most 50 nm and otherwise is less than 5% in the whole wavelength range.

Alternatively, it is also possible to illuminate the surgical region using an illumination unit which has optical elements, the resultant spectral transmission of which has a first pass region which is matched to the fluorescence excitation spectrum of the dye and comprises a second pass region for wavelengths which lie between the wavelengths of the fluorescence excitation spectrum and the wavelengths of the fluorescence spectrum. The spectral transmission of the observation filter must then have a first pass region, which is matched to the fluorescence spectrum of the dye, and a second pass region, which lies in the same wavelength range as the second pass region of the illumination unit. Here too, it is advantageous if the degree of spectral transmission of the resultant spectral transmission of the overall system consisting of the illumination unit and the observation filter is more than 5% only in a narrow wavelength range of at most 50 nm, but is otherwise less than 5% in the whole wavelength range.

Thus, it is expedient if the illumination unit provides no illumination light or only little illumination light at least in a wavelength range of the fluorescence bands of the dye. In particular, it is expedient for the illumination unit to contain at least one filter for setting the wavelength range for the fluorescence excitation of the dye. It is advantageous if this filter at least partly filters out light whose wavelength lies outside of the fluorescence bands of the dye. In particular, it is advantageous if the filter at least partly filters out light with a wavelength lying in the fluorescence bands of the dye PPIX and/or sodium fluorescein and/or hypericin. The electronic detection unit capturing the light from at least one object point preferably contains a filter which at least partly filters out light in the wavelength range of the excitation bands of the dye. It is expedient if, for filtering-out purposes, provision is made for a filter which is opaque to light in the wavelength range of the excitation bands of the dye PPIX and/or sodium fluorescein and/or hypericin. By way of example, the system can be integrated into a surgical microscope.

A concept of the invention also relates to positionally correctly correlating the color coordinate information ("0", "1") calculated by the computer unit with patient data which are obtained pre-surgery.

Moreover, the invention relates to a computer program for a computer unit for controlling the visualization apparatus in a system according to the invention. Moreover, the invention relates to a method for visualizing characteristic tissue in a surgical region, in which the color coordinate of the light from at least one object point is established in a color space, in which the established color coordinate is compared to a reference color coordinate in the color space, and in which color information which can be displayed on a visualization device is calculated from the comparison of the established color space with the reference color coordinate. In particular, this color information can be used for controlling display information visualized by means of the visualization device.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
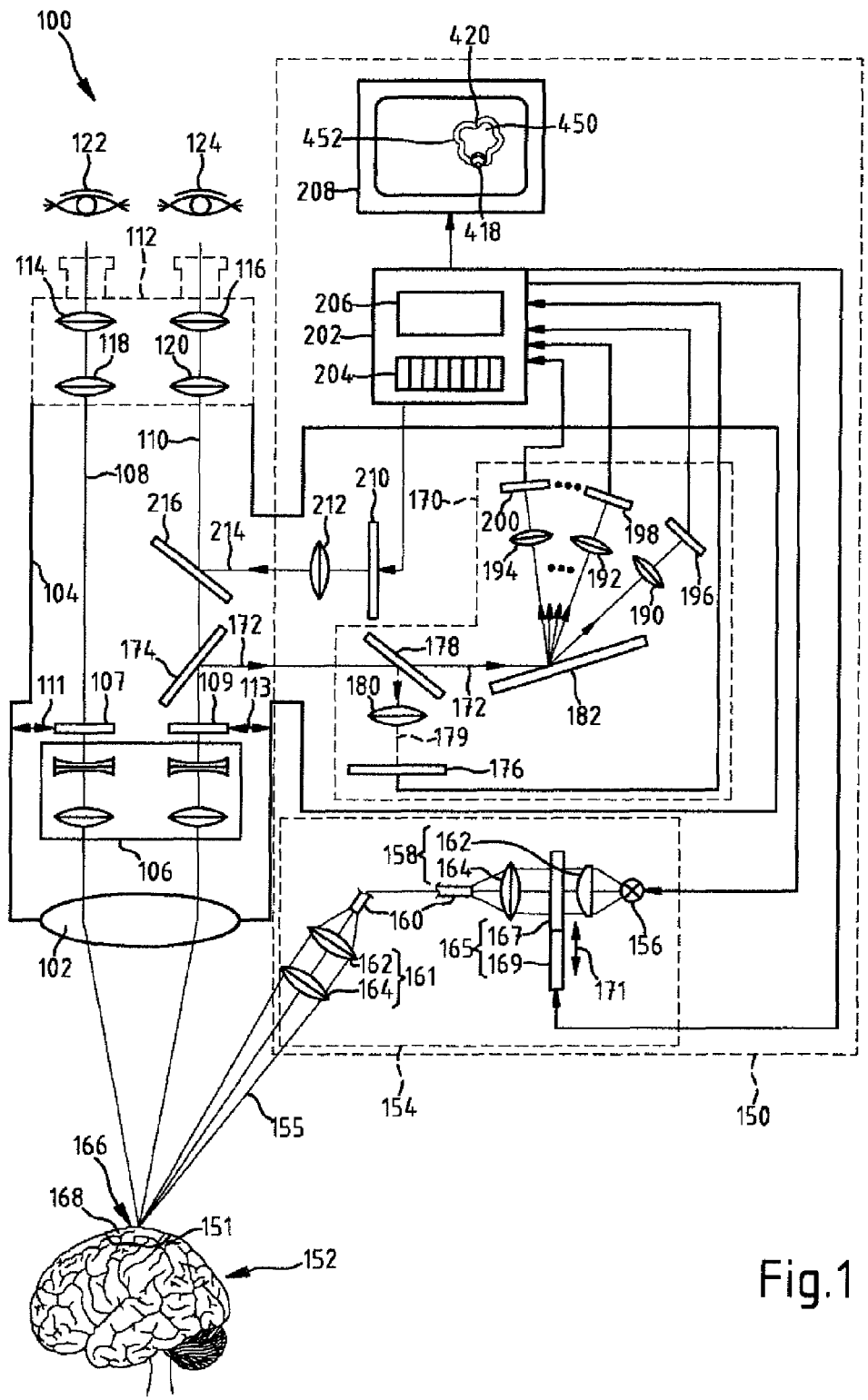
FIG. 1 is a schematic of a surgical microscope with a system for visualizing tissue in a surgical region.

FIG. 1 shows a surgical microscope 100 with a system 150 for visualizing characteristic tissue in a surgical region 152. The surgical microscope 100 is designed for neurosurgical operations. The surgical microscope 100 has a microscope main objective 102. The microscope main objective 102 is held in a microscope main body 104. The microscope main body 104 contains an adjustable magnification system 106. A left-hand and a right-hand observation beam path (108, 110) passes through the microscope main objective 102. A binocular tube 112 is connected to a microscope main body 104. In the left-hand and right-hand observation beam paths (108, 110), the binocular tube 112 contains an eyepiece lens (114, 116) and a tube lens (118, 120). The binocular tube 112 allows an observer to observe an area 151 in the surgical region 152 stereoscopically using a left-hand and right-hand observer eye (122, 124).

The visualization system 150 comprises an illumination unit 154. The illumination unit 154 provides illumination light for the surgical region 152 via an illumination beam path 155. The illumination unit 154 comprises a xenon light source 156. The illumination unit 154 contains further optical elements in the form of a lens system 158, an optical waveguide 160 and an illumination lens 161. The light from the xenon light source 156 is coupled into an optical waveguide 160 via a lens system 158. From the optical waveguide 160, illumination light reaches the surgical region 152 through an illumination lens 161 with lens elements (162, 164).

The illumination unit 154 contains a filter assembly 165 for setting the spectral composition of the illumination light. The filter assembly 165 can be switched. It contains a first illumination filter 167 and a second illumination filter 169. The illumination filters (167, 169) can be moved into and out of the illumination beam path 155 in accordance with the arrow 171.

The illumination filter 167 is a band pass filter. It transmits light from the xenon light source 156 in the spectral range between 390 nm and 410 nm, preferably in the spectral range between 390 nm and 430 nm. By contrast, light in the spectral range below 390 nm and above 410 nm is filtered out or strongly suppressed by the illumination filter 167.

The illumination filter 169 is a heat protection filter. This heat protection filter is substantially opaque to light from the xenon light source 156 with a wavelength of greater than 800 nm. This filter transmits light in the visible spectral range with a wavelength of below 800 nm.

In the microscope main body 104 there is, on the end of the magnification system 106 facing away from the microscope main objective 102, an observation filter 107 for the left-hand observation beam path 108 and an observation filter 109 for the right-hand observation beam path 110. In accordance with the double-headed arrows (111, 113), the observation filters (107, 109) can be moved into or out of the observation beam path (108, 110). The illumination filter 167 on the one hand and the observation filters (107, 109) on the other hand have a filter characteristic which is matched to one another. For the purposes of observing the surgical region 152 with fluorescence light, the illumination filter 167 is switched into the illumination beam path 155 and the observation filters (107, 109) are arranged in the observation beam paths (108, 110).

Figure 2:
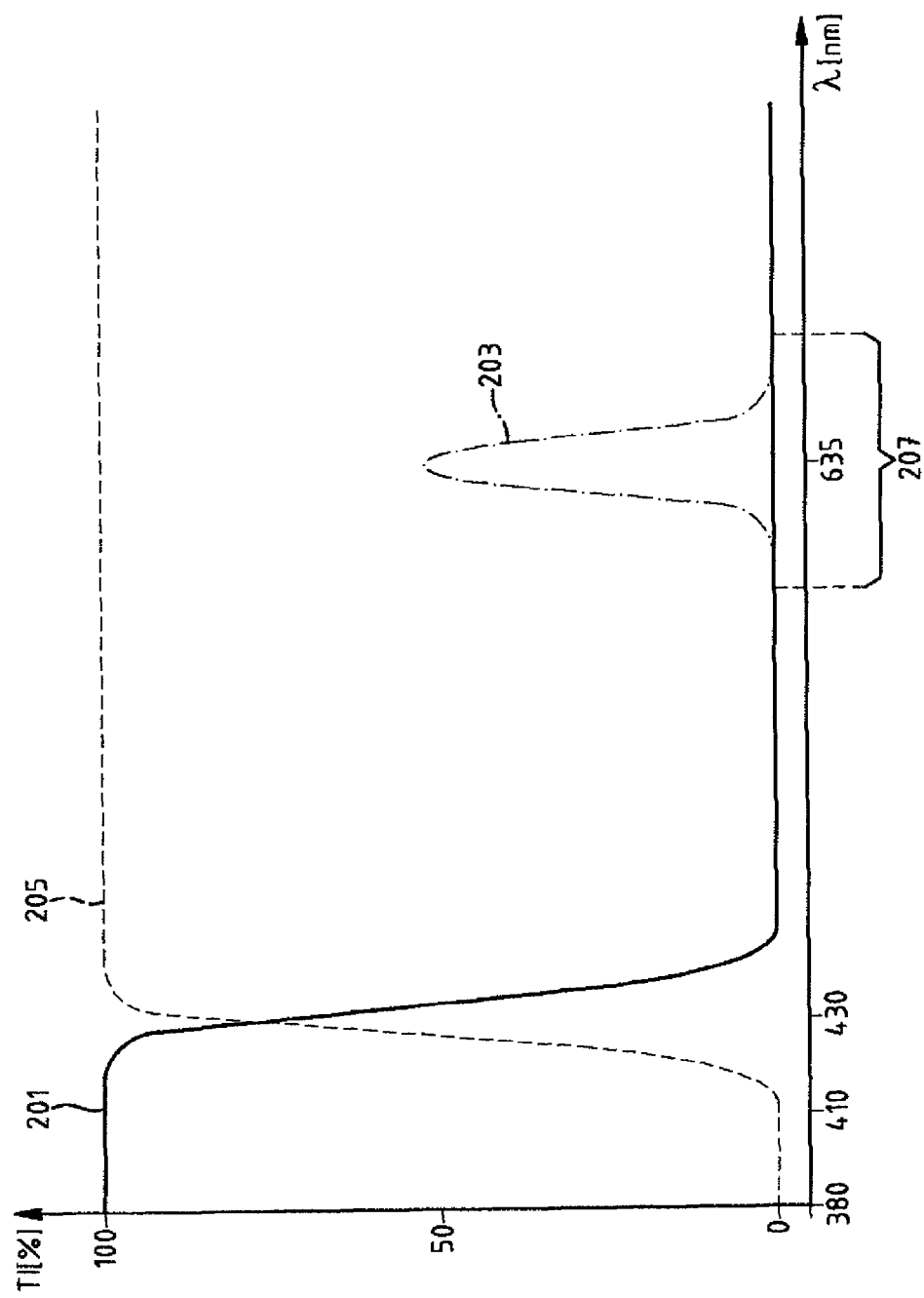
FIG. 2 shows the spectral transmissions $TI_{B1}(\lambda)$ and $TI_{D1}(\lambda)$ of the optical elements of an illumination unit and an observation filter in the surgical microscope.

FIG. 2 shows, as curve 201, the resultant spectral transmission $TI_{B1}$ ($\lambda$) of the optical elements in the illumination unit 154, via which the illumination light is provided, if the illumination filter 167 is located in the illumination beam path. The resultant spectral transmission $TI_{B1}$ ($\lambda$) of the optical elements of the illumination unit 154 is matched to the fluorescence excitation spectrum of a dye which can be accumulated in the body tissue in the surgical region. The resultant spectral transmission $TI_{B1}$ ($\lambda$) of the optical elements in the illumination unit 154, shown in FIG. 2 by means of curve 201, is suitable for fluorescence observation using the dye PPIX.

The optical elements of the illumination unit 154 can naturally also be configured for a resultant spectral transmission $TI_{B1}$ ($\lambda$) which is suitable for fluorescence observation using other dyes, for example for fluorescence observation using sodium fluorescein or hypericin.

The illumination filter 167 dominates the profile of the resultant spectral transmission $TI_{B1}$ ($\lambda$) of the optical elements in the illumination unit 154. It ensures that the illumination unit 154 illuminates the surgical region 152 only with light from which the wavelength range 207 of the corresponding fluorescence light specific to the dye has been filtered out.

Figure 3:
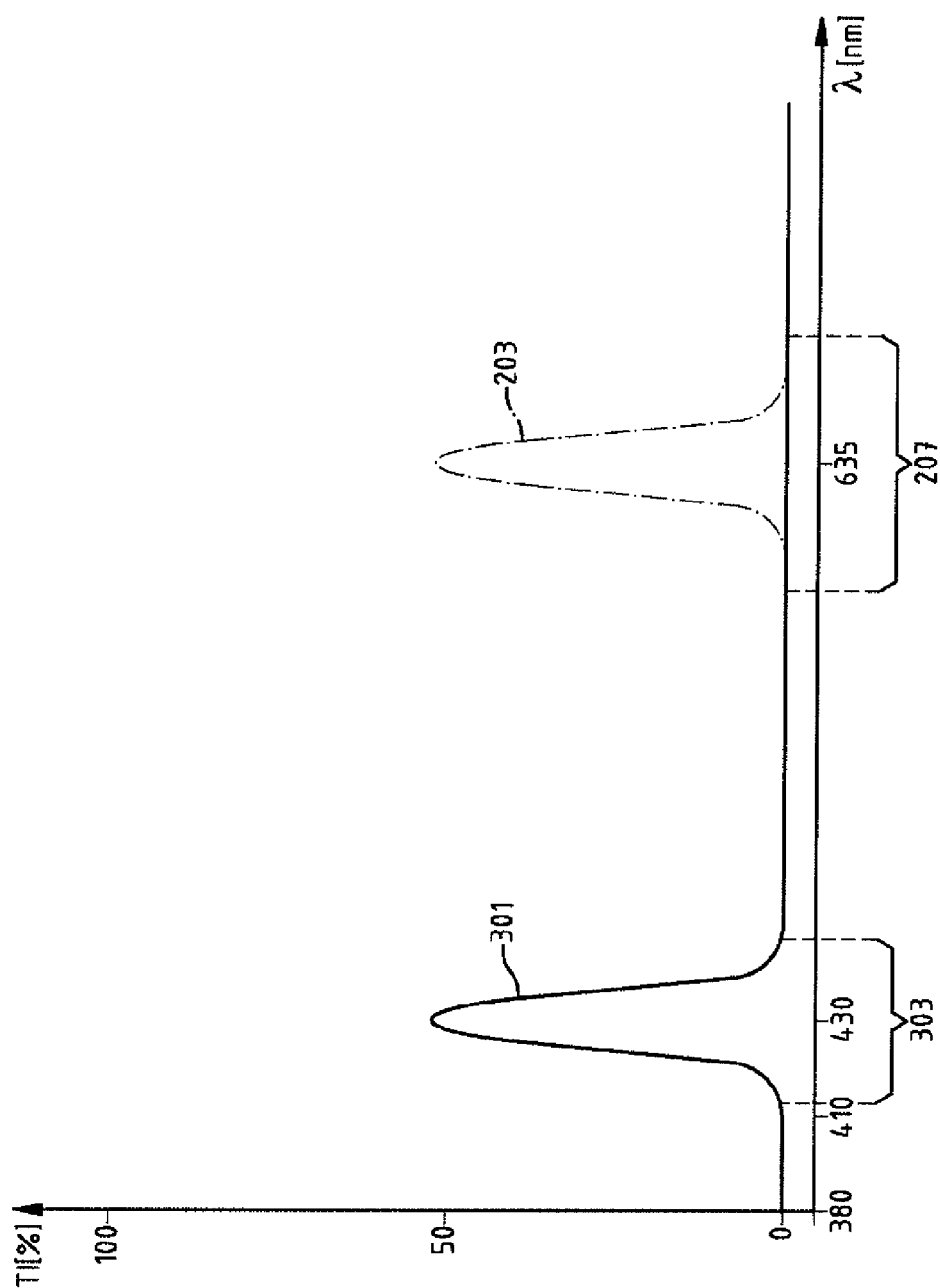
FIG. 3 shows the resultant spectral transmission $TI_{G1}$ ($\lambda$) of the overall system formed in the surgical microscope by the illumination unit and the observation filter.

The curve 205 in FIG. 2 shows the resultant spectral transmission $TI_{D1}$ ($\lambda$) of the optical elements in the observation beam path of the surgical microscope 100. This resultant spectral transmission $TI_{D1}$ ($\lambda$) is defined by the observation filters (107, 109). The profile of the spectral transmission $TI_{D1}$ ($\lambda$) of the observation filters (107, 109) is such that a degree of spectral transmission of the resultant spectral transmission $TI_{G1}$ ($\lambda$), shown using curve 301 in FIG. 3, of the overall system consisting of the illumination unit 154 and the observation filter 109 is more than 5% only in a wavelength range 303, which extends over at most 50 nm, and is less than 5% outside of this wavelength range.

Figure 4:
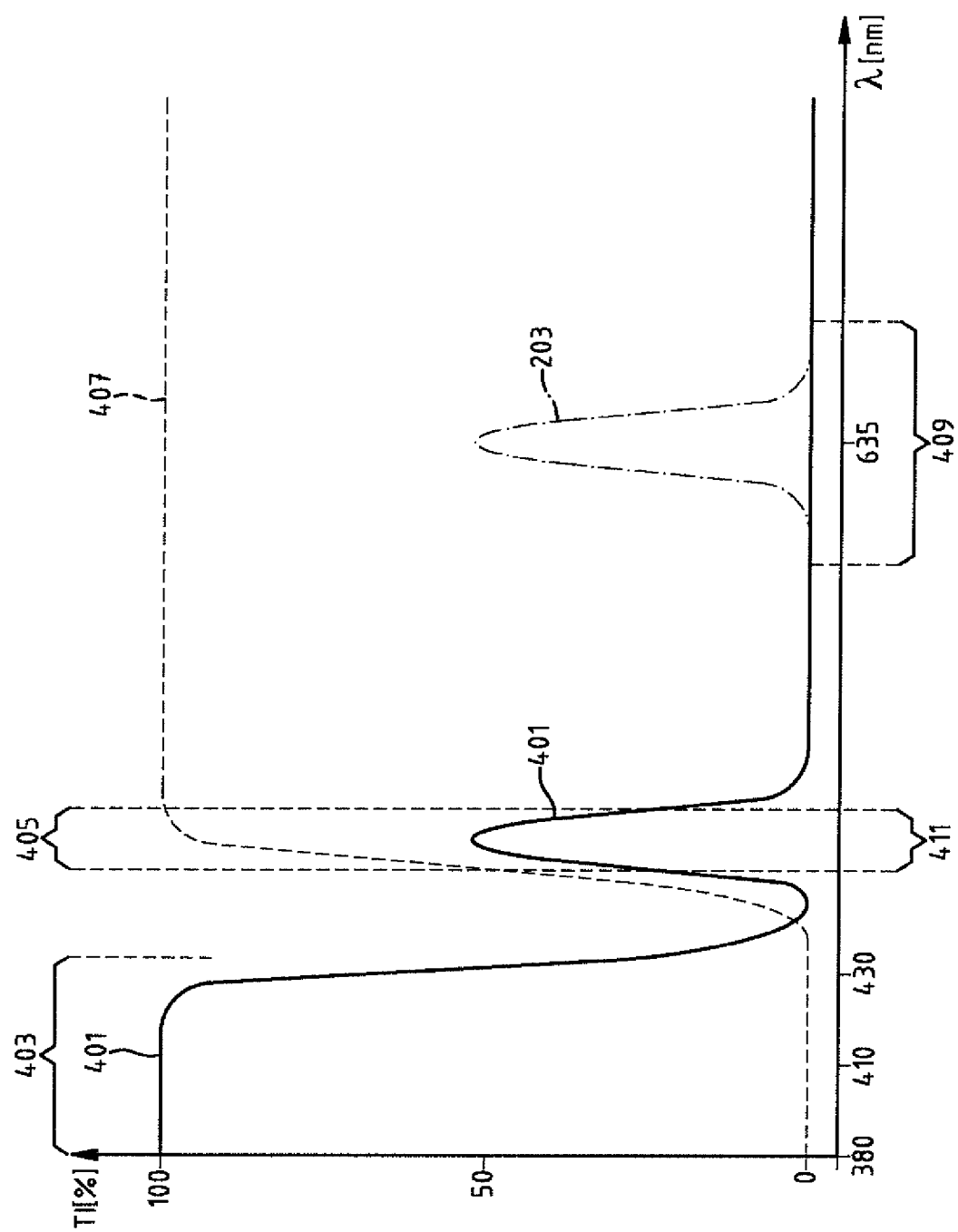
FIG. 4 shows an alternative embodiment of the spectral transmissions $TI_{B2}$ ($\lambda$) and $TI_{D2}$ ($\lambda$) of the optical elements of the illumination unit and the observation filter in the surgical microscope.

In order to enable fluorescence observation, the illumination filter 167 in the illumination unit 154 can also be embodied in such a way that the resultant spectral transmission of the optical elements in the illumination unit corresponds to the curve 401, shown in FIG. 4, when the illumination filter 167 is situated in the illumination beam path.

Here the resultant spectral transmission $TI_{B2}(\lambda)$ has a pass region 403. The pass region 403 is matched to the fluorescence excitation spectrum of body tissue in which the dye PPIX has accumulated.

The resultant spectral transmission $TI_{B2}(\lambda)$ of the optical elements in the illumination unit 154, shown using curve 401 in FIG. 4, is likewise suitable for fluorescence observation using the dye PPIX. The optical elements of the illumination unit 154 can naturally also be configured for a resultant spectral transmission $TI_{B2}(\lambda)$ which is suitable for fluorescence observation using other dyes, for example for fluorescence observation using sodium fluorescein or hypericin.

The resultant spectral transmission $TI_{B2}(\lambda)$ has a second pass region 405, the wavelengths of which lie between the wavelengths of the fluorescence excitation spectrum and the wavelengths of the fluorescence spectrum of the dye PPIX.

Figure 5:
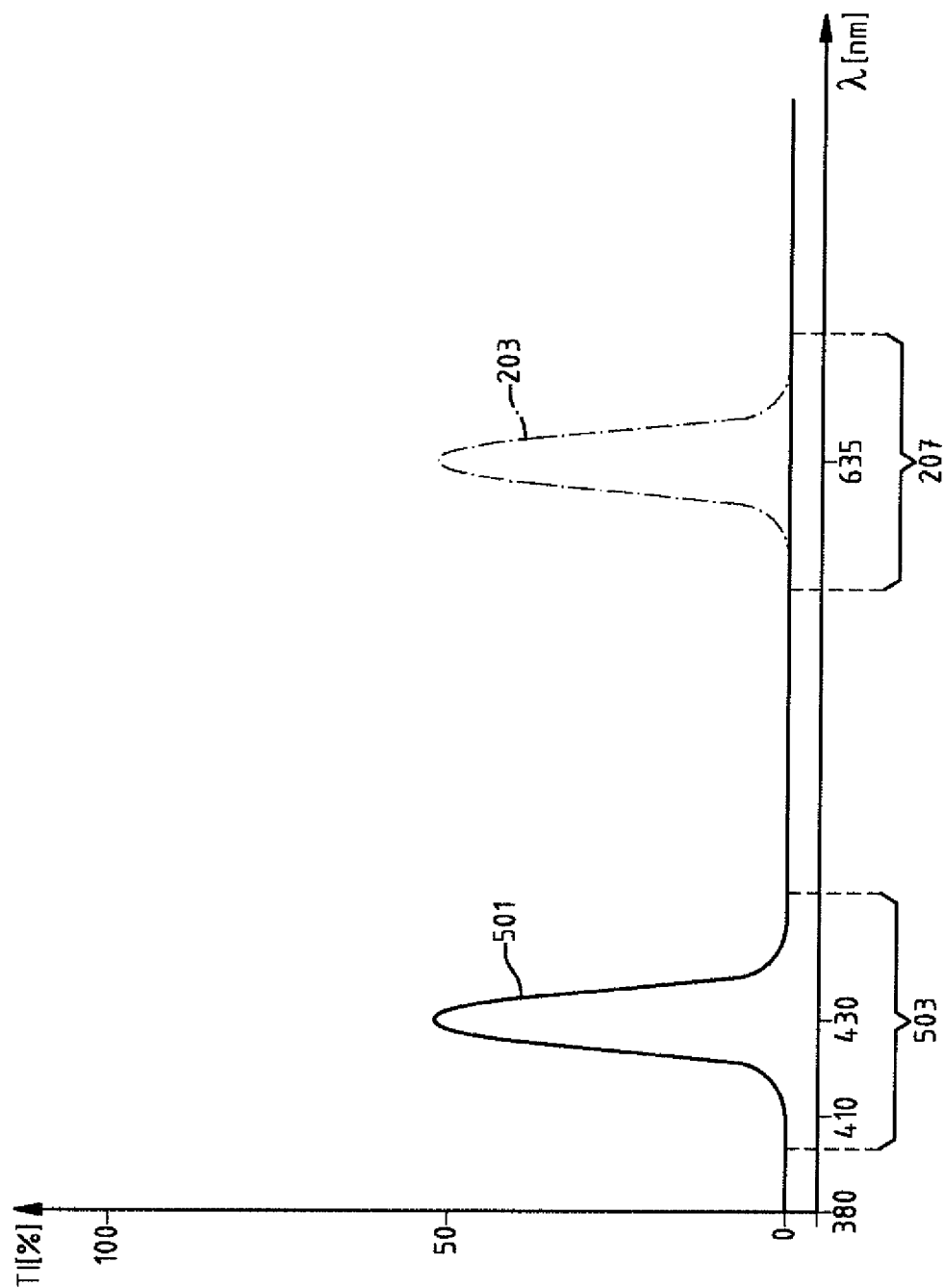
FIG. 5 shows the resultant spectral transmission $TI_{G2}$ ($\lambda$) of the alternative embodiment of the overall system formed in the surgical microscope by the illumination unit and the observation filter.

In this case, the viewing or observation filters (107, 109), which set the resultant spectral transmission of the optical elements in the observation beam path, also have a spectral transmission $TI_{D2}(\lambda)$ corresponding to the curve 407. The spectral transmission $TI_{D2}(\lambda)$ has a first pass region 409 matched to the fluorescence spectrum of body tissue in which the dye PPIX has accumulated and which can be examined using the surgical microscope 100. Moreover, the spectral transmission $TI_{B2}(\lambda)$ has a second pass region 411 which lies in the same wavelength range as the second pass region 405 of the illumination unit 154. Here too, the spectral transmission $TI_{D2}(\lambda)$ of the observation filters (107, 109) corresponding to the profile of the curve 407 in FIG. 4 is such that a degree of spectral transmission of the resultant spectral transmission $TI_{G2}(\lambda)$, shown using curve 501 in FIG. 5, of the overall system consisting of the illumination unit 154 and the observation filter 109 is more than 5% only in a wavelength range 503, which extends over at most 50 nm, and is less than 5% outside of this wavelength range.

When using other fluorescence dyes in a surgical region, it is necessary for this second pass region 405 in the resultant spectral transmission $TI_{B2}(\lambda)$ of the optical elements of the illumination unit 154 and the pass regions (409, 411) in the spectral transmission $TI_{D2}(\lambda)$ of the observation filters (107, 109) to be correspondingly matched to other wavelengths.

The visualization system 150 in the surgical microscope 100 from FIG. 1 comprises a detection unit 170 in order to capture light 166 from an object point 168 in the surgical region 152. Observation light from the region in the surgical region 152 can be supplied from the right-hand observation beam path 110 with an optical axis 172 to the detection unit 170 through the observation filter 109 via a decoupling beam splitter 174. There is an image sensor 176 in the detection unit 170. This image sensor 176 receives observation light with a beam path 179 which is guided through a positive lens element 180 and a beam splitter 178.

There is a reflection grating 182 in the detection unit 170. The reflection grating 182 acts as a spectrometer. The reflection grating 182 receives the observation light along the optical axis 172 with a parallel beam path which passes through the beam splitter 178. The reflection grating 182 is used for spectral decomposition of the illumination light in the detection unit 170. The reflection grating 182 reflects the observation light from the observation beam path 110 in a wavelength-selective fashion in different directions along the optical axes (195, 197, . . . 199) to a multiplicity of image sensors (196, 198, . . . 200). The observation light reflected to the image sensors (196, 198, . . . 200) is focused there by positive lens elements (190, 192, . . . 194). Hence, the image sensors (196, 198, . . . , 200) can be used to detect the image of the area 151 of the surgical region 152 with an object point 168 in different spectral ranges.

The image sensors (196, 198, . . . 200) of the detection unit 170 are connected to a computer unit 202. The computer unit 202 comprises an input unit 204 and contains program storage means 206. The computer unit 202 is connected to a touch-sensitive screen 208. The computer unit 202 controls a display 210. What is displayed by the display 210 is superposed onto the observation light in the right-hand observation beam path 110 via a lens element 212 with a beam path 214 through a beam splitter 216. An observer can thereby simultaneously see what is displayed on the display 210 and the area 151 of the surgical region 152 in the right-hand eyepiece eye lens of the binocular tube.

When the illumination filter 167 is switched into the illumination beam path 155, the light from the illumination unit 154 can excite the dye PPIX to fluoresce as well. This dye accumulates in tissue afflicted by the tumor in the brain of a patient when the medicament Gliolan is administered to the patient. The medicament Gliolan contains the substance 5ALA.

Figure 6:
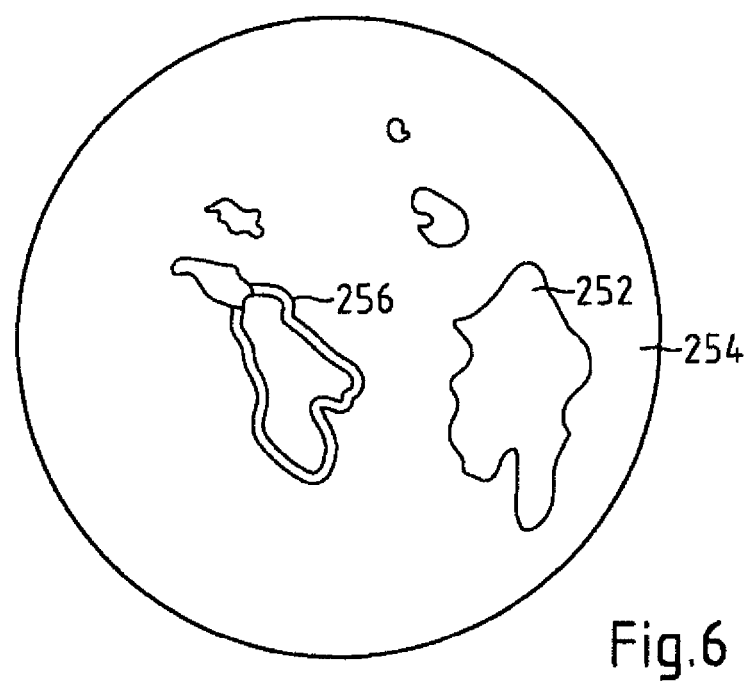
FIG. 6 shows the image in the surgical microscope of a surgical region with tumor tissue.

FIG. 6 shows the image of the surgical region 152 with fluorescent tumor tissue for an observer in the binocular tube 112 of the surgical microscope 100. When illuminated with light having a wavelength $\lambda$=400 nm, tumor-diseased tissue 252 fluoresces with a red color in the surgical region 152. An observer perceives healthy tissue 254 as having blue color in the eyepiece eye lens of the binocular tube 112. The edge regions 256 of tumor-afflicted tissue 252, in which infiltrated tumor cells are situated, usually have a mixed color for an observer. The mixed color is perceived to be salmon or else pink by very many persons. It has a hue lying between the hue blue and the hue red.

The complete removal of the tumor in tumor surgery is decisive for the success of the cure of a patient suffering from a brain tumor. Here it is important that a surgeon can also reliably identify the edge regions of the tumor. However, it is difficult for the surgeon to capture edge regions of a tumor during a neurosurgical operation. Illumination of the surgical region with white illumination light is necessary during the resection of tissue material. The vessels in the tissue of the human brain in particular can be identified in white illumination light. However, fluorescing tumor tissue is not readily visible to a surgeon in white illumination light. In order to be able to see tumor-diseased tissue clearly, the surgeon needs to illuminate the surgical region with light in the spectral range between 390 nm and 410 nm. However, the surgeon cannot identify any vessels in the surgical region in this type of illumination. As a result of this, a resection of tissue is connected with great risks to the patient at this point.

Figure 7:
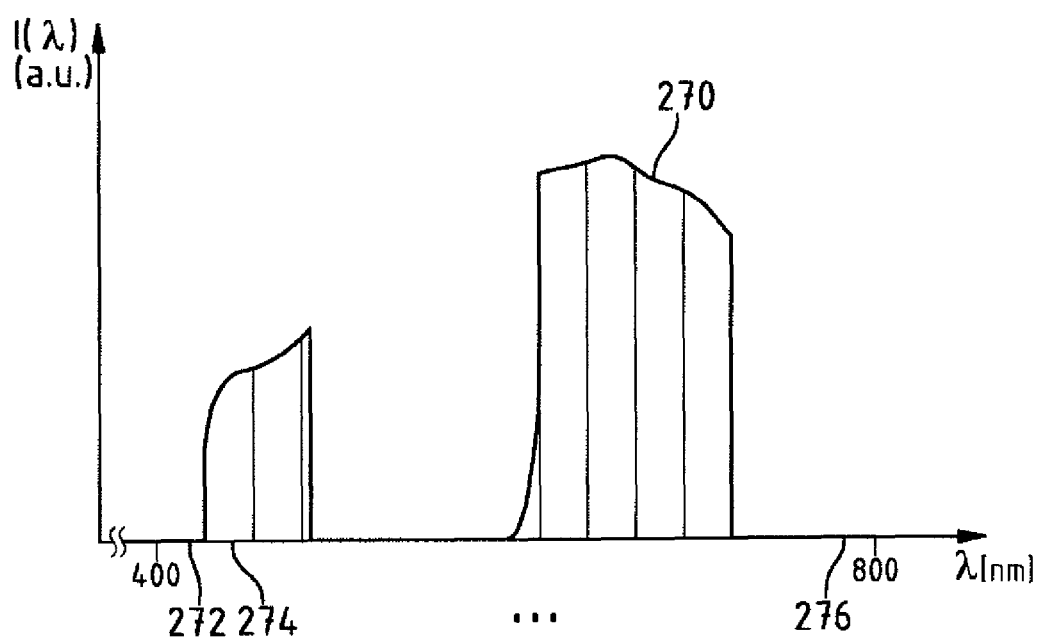
FIG. 7 shows a spectral intensity distribution, captured by a detection unit in the surgical microscope, of the light, in the surgical region, originating from an object point.

FIG. 7 shows the intensity distribution 270, captured by the detection unit 170, for the light 166 of an object point 168 in the area 151 of the surgical region 152 captured by the surgical microscope 100. By means of the image sensors (196, 198, . . . , 200), the light from the object points in the area 151 of the surgical region 152 is captured in respective different spectral ranges (272, 274, . . . , 276). The spectral ranges (272, 274, . . . , 276) cover the wavelength range between 400 nm and 800 nm.

Figure 8:
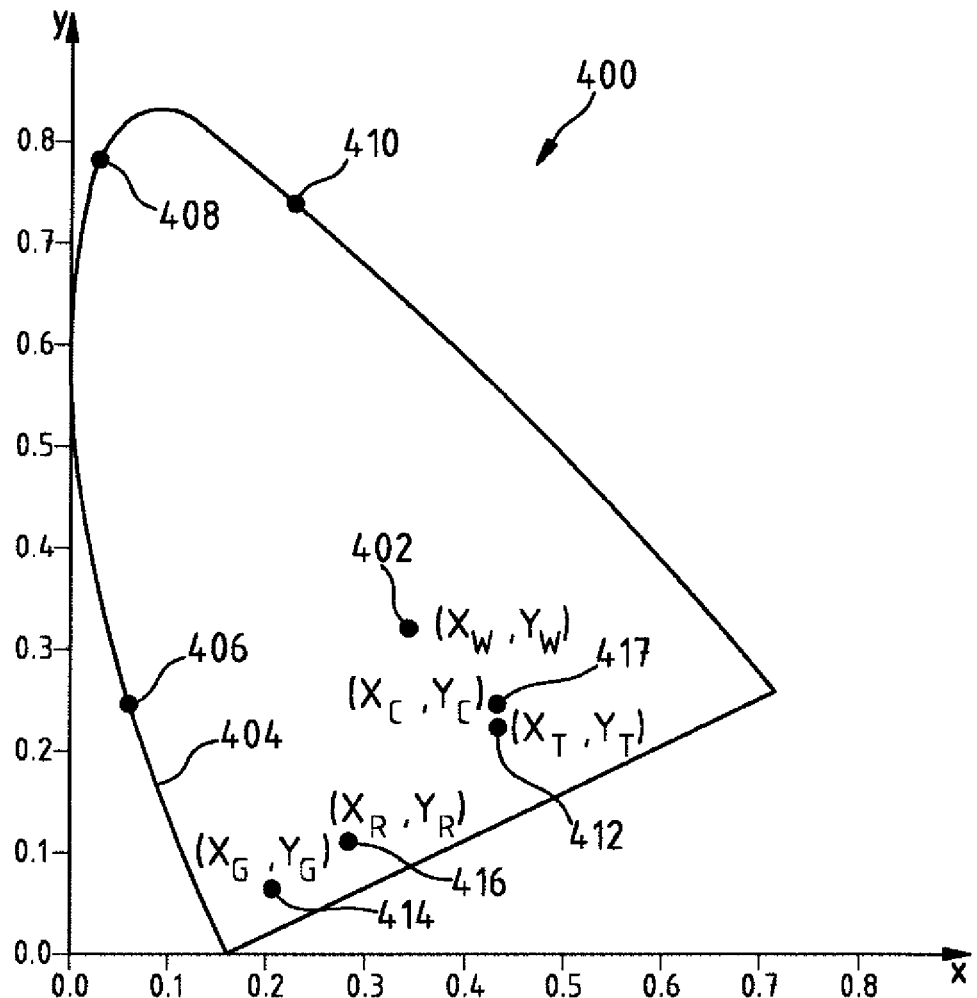
FIG. 8 shows the color coordinate in the color space CIE $D_{65}$ of object points, calculated by a computer unit in the surgical microscope.

FIG. 8 shows the color space CIE $D_{65}$. The color space CIE $D_{65}$ is a two-dimensional region 400. A color coordinate is a point in the two-dimensional region 400. The color coordinate in the two-dimensional region 400 is defined precisely by a number tuple (x, y). The region 400 is delimited by an edge curve 404. The points (406, 408, 410) lying on the edge curve 404 correspond to color coordinates for monochromatic light. Color coordinates in the interior of the region 400 are based on light with a wavelength mixture. The color coordinate CIE $D_{65}$ corresponding to the number tuple $(x_W, y_W)$ for the white point 402 lies in the interior of the two-dimensional region 400.

In the color space CIE $D_{65}$, the fluorescence light, perceived as being reddish by an observer, of tumor cells in the human brain, in which the dye PPIX has accumulated, has the color coordinate defined by the number tuple $(x_T, y_T)$. Regions of the human brain in which there are no tumor cells have the color coordinate 414 corresponding to the number tuple $(x_G, y_G)$ in the color space CIE $D_{65}$ when illuminated with blue light having a wavelength of 400 nm. The fluorescence light from the edge regions of a tumor region in the human brain, which fluorescence light is perceived as being salmon by many persons, has a color coordinate 416, which is described by the number tuple $(x_R, y_R)$, in the color space CIE $D_{65}$.

Thus, in the color space CIE $D_{65}$, the color coordinates 412, 414 and 416, which correspond to healthy tissue, tumor-afflicted tissue and tissue from the edge regions of a tumor, are spaced far apart and have a large geometric distance.

Using the visualization device 150 in the surgical microscope 100 from FIG. 1, it is possible to display tumor-afflicted tissue reliably for an observer on the screen 208 and the display 210. To this end, for each pixel, captured by the image sensors (196, 198, . . . 200) of an object point 168, the computer unit 202 establishes the coordinates (x, y) of the color coordinate for each object point captured by means of the image sensors (196, 200). The computer unit in each case compares these color coordinates to a reference color coordinate 417, shown in FIG. 8, which has the coordinates $(x_c, y_c)$ of a color coordinate, typical for the edge region of tumor tissue, in the color space 400. If a distance norm $\Delta E := \|(x,y); (x_c,y_c)\|$ relating to the color distance defined in DIN 5033 part 2 between the color of an object point (x, y) and the color of a reference point $(x_c, y_c)$ exceeds a threshold $A_S$, the color coordinate information "0" is associated with this object point. However, if $\Delta E \leq A_S$ applies, the color coordinate information "1" is assigned to a pixel. By way of example, such a distance norm $\|(x,y); (x_c,y_c)\|$ for the color coordinates can be defined as follows: $\Delta E := \sqrt{(x-x_c)^2 + (y-y_c)^2}$. This distance norm corresponds to the geometric displacement of the color coordinate, captured for an object point, in the color space CIE $D_{65}$ from the reference color coordinate 417.

In the surgical microscope 100 in FIG. 1, the pixels provided with the color coordinate information "1" are, by means of the computer unit 202, displayed on the display 210 and the touch-sensitive screen 208 with a uniform marking color. By virtue of the color coordinate of the light emerging from object points that are situated in the edge region 450 of a tumor region being selected as reference color coordinate $(x_c, y_c)$, the edge region of a region with tumor-diseased tissue can be visualized with a clear and easily visible edge 452 as display information 420.

A setting mode is provided in the surgical microscope 100 in FIG. 1 in order to set a reference color coordinate 417 with the coordinates $(x_c, y_c)$. The setting mode allows an observer, by touching a region 418 on the touch-sensitive screen 208, to select, that is, predetermine, on the screen display as a reference color coordinate $(x_c, y_c)$ the color coordinate of the observation light based on this region. The selection of a plurality of reference color coordinates is possible in the setting mode. By way of example, it is possible to select a reference color coordinate for tumor tissue, a reference color coordinate for healthy tissue and a color coordinate for the edge region of a tumor.

Figure 9:
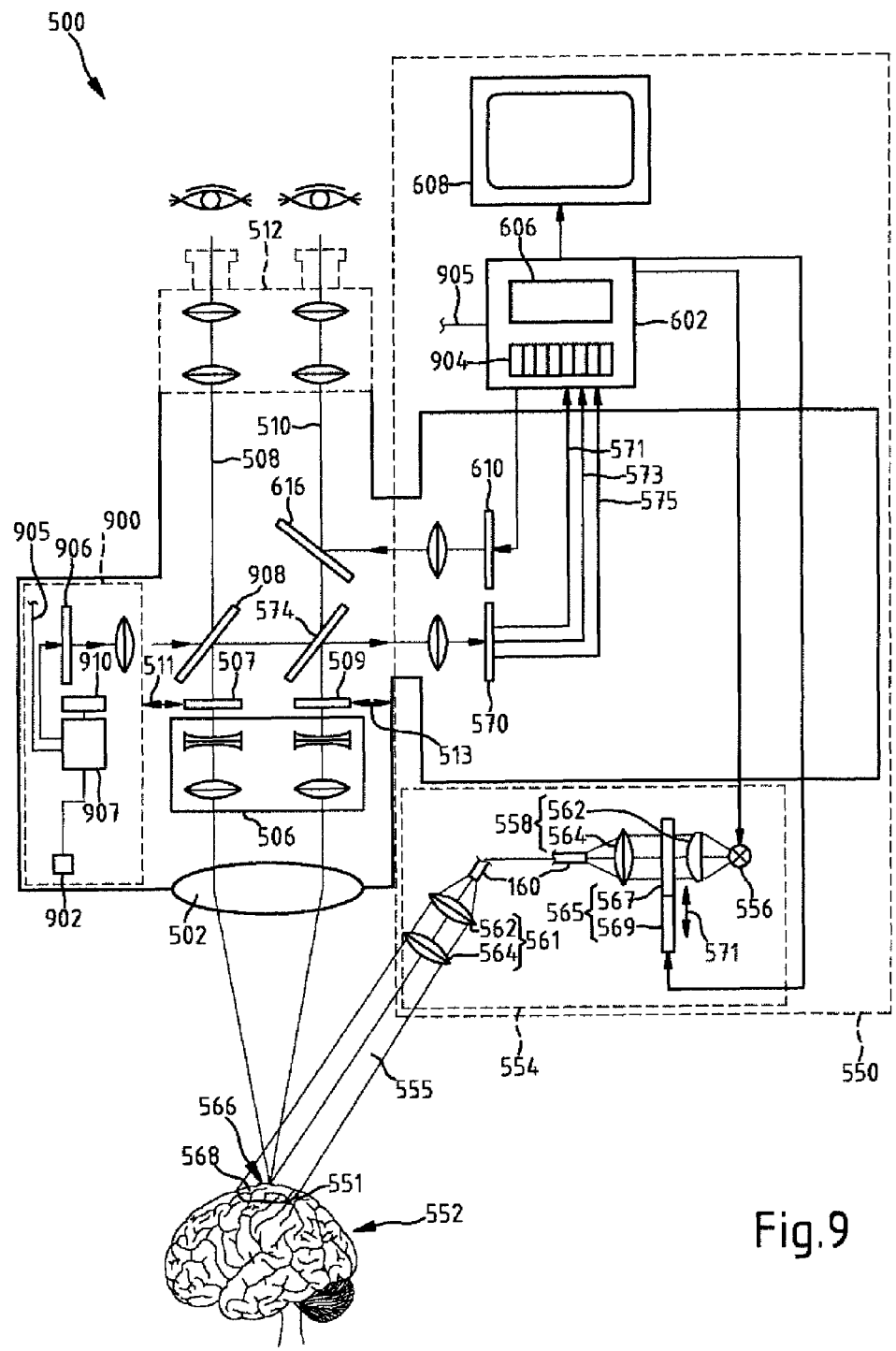
FIG. 9 shows a further surgical microscope with a system for visualizing tissue in a surgical region; and, FIG. 10 shows the color coordinate in the RGB color space of object points in an object region visualized by the surgical microscope.

FIG. 9 shows a surgical microscope 500 with a system 550 for visualizing characteristic tissue in a surgical region 552. Modules in the surgical microscope 500 which are identical to modules in the surgical microscope 100 from FIG. 1 are in this case provided with reference numerals which have been increased by 400 compared to FIG. 1.

The surgical microscope 500 contains a color camera as detection unit 570 for capturing light 566 from an object point 568 in the surgical region 552. The color camera has a red color channel 571, a blue color channel 573 and a green color channel 575. The signal (R, G, B) of the red, green and blue color channels (571, 573, 575) of the color camera is fed as RGB signal triplet to the computer unit 602 for determining the color coordinate of an object point 568 in the region 551 of the surgical region 552, which can be captured by the surgical microscope 500.

For each object point 568 in the surgical region 552, the computer unit 602 determines the color coordinate in the CIE RGB color space. It then calculates the ratio R/B for the RGB signal triplet (R, G, B).

Figure 10:
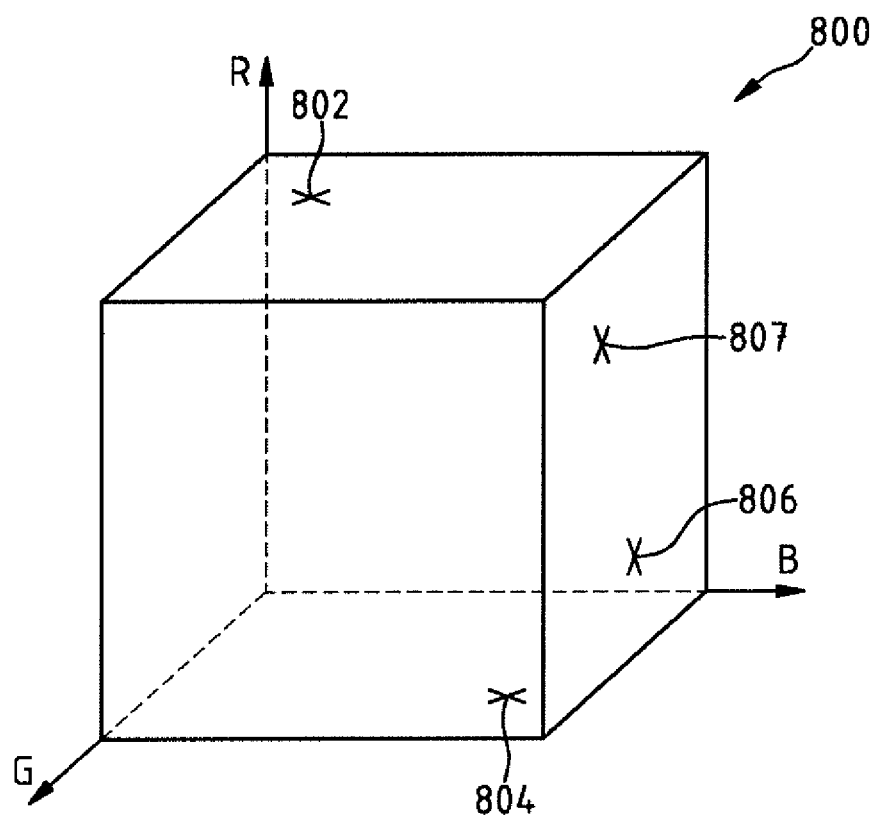

FIG. 10 shows the CIE RGB color space with a color coordinate 802 for the light of an object point localized in the tumor tissue. The color coordinate 804 corresponds to light from an object point in healthy tissue. The color coordinate 806 resorts to the light from an object point, which is situated in a region with healthy tissue in the surgical region, which tumor cells have infiltrated. As in the surgical microscope 100 of FIG. 1, the color coordinates (802, 804, 806) for light from the surgical region based on object points in pathologically different tissue are spatially separated from one another in the color space 800 as well.

For the color coordinate of an object point, the computer unit 602 compares the ratio R/B as information relating to the color coordinate of this object point with a threshold $S_a$. From this, the computer unit 602 determines color coordinate information for this object point. If the ratio R/B exceeds the threshold $S_a$, the object point is associated with the color coordinate information "0". If R/B $\leq S_a$ applies to the ratio, the color information "1" is assigned to the object point. The threshold $S_a$ can be set by an observer via the input unit 904 of the computer unit 602.

In order, for example, to visualize the edge region of tumor-afflicted tissue, the threshold $S_a$ is set to the ratio R/B as information relating to the color coordinate for salmon light.

The surgical microscope 500 contains an apparatus 900, by means of which patient data obtained pre-surgery, for example, magnetic resonance imaging data or computed tomography data, can be superimposed in the correct spatial position on the object image in the observation beam path 508 and on the screen 608. The apparatus 900 contains a position sensor 902. The position sensor 902 captures the spatial position of the surgical microscope 500 relative to the object area 552. The position sensor 902 is connected to a computer unit 907 in the apparatus 900. The computer unit 907 controls a display 906. What is displayed on the display 906 is mirrored into the observation beam path 508 via a beam splitter 908. As a result of the spatial position, captured by the position sensor 902, of the surgical microscope 500 relative to the surgical region 552, the computer unit 907 calculates a spatially correct display on the display 906 of patient data from a data storage medium 910. The apparatus 900 is connected to the computer unit 602 via a bidirectional data link 905.

The position and the spatial extent of tumor-diseased tissue can change during the course of a surgical operation on the human brain. In this case, there are spatial deviations between the patient data obtained pre-surgery, which can be visualized by means of the apparatus 900, and the structure of a tumor in the surgical region.

The computer unit 602 therefore contains a correlation program in the program storage medium 606. This correlation program renders it possible to capture the displacement and deformation of a tumor region in the surgical region by correlating the profile, established by determining the color coordinate in the color space 800, of the color coordinate information, assigned to the pixels of objects points in the surgical region, with the patient data obtained pre-surgery. To this end, an observer sets the threshold $S_a$ to the ratio R/B which is given for the typical color of light from the edge region of a tumor at the reference color coordinate 807 in FIG. 10. The correlation program then correlates the color information corresponding to the edge region of a tumor with the obtained patient data. The data obtained pre-surgery is thereupon corrected and displayed on the screen 608 and the display 610 of the surgical microscope, together with the image of the object area 552.

It should be noted that, in principle, it is also possible to determine the color coordinate for an object point in the surgical microscope using a black/white camera. However, in order to determine color coordinates in a color space for the light from object points in the surgical region, the operation region must then be illuminated sequentially in time, for example using light colored red (R), green (G) and blue (B).

In conclusion, the following preferred features of the invention should be noted: A system (150, 550) for visualizing characteristic tissue with dye in a surgical region (152, 552) contains a detection unit (170, 570) capturing light from at least one object point (168, 568). The system (150, 550) comprises a computer unit (202, 602), connected to the detection unit (170, 570), for actuating a visualization apparatus (208, 210, 608, 610) displaying an image of a region in the surgical region (152, 552). The computer unit (202, 602) establishes the color coordinate (412, 414, 416) in a color space 400 for the light from the at least one object point (168, 568) in the surgical region (152, 552). It calculates color coordinate information ("0", "1") for controlling the visualization apparatus (208, 210, 608, 610) depending on the position of the color coordinate (412, 414, 416, 802, 804, 806) established for the object point (168, 568) by comparing information relating to the established color coordinate (412, 414, 416, 802, 804, 806) of the object point (168, 568) with information relating to a characteristic reference color coordinate.

It is understood that the foregoing description is that of the preferred embodiments of the invention and that various changes and modifications may be made thereto without departing from the spirit and scope of the invention as defined in the appended claims.

What is claimed is:

1. A system for visualizing characteristic tissue in a surgical region to determine an edge region of tumor tissue in a human brain, the system comprising:
a detection unit including at least one sensor and configured to detect light from an object point (x, y) in said surgical region;
a computer unit connected to said detection unit and having a computer processor;
a visualization unit having a display and being driven by said computer unit and configured to display unevaluated information defined by an image of an area within said surgical region;
said computer unit including a non-transitory computer readable storage medium having program code stored therein;
said computer processor being configured to run said program code;
said computer unit being configured to determine a color coordinate having a position in a color region as to said light from said object point (x, y);
said computer unit being further configured to compute, in dependence upon said position of the determined color coordinate in said color region, a two state digital color coordinate information ("0", "1") for controlling said visualization unit by comparing information as to said determined color coordinate to a characteristic reference color coordinate ($x_c$, $y_c$) typical for said edge region of said tumor tissue in said color region in accordance with said program code wherein said two state digital color coordinate information ("0", "1") can have a first state ("0") or a second state ("1") and wherein said color coordinate information ("0", "1") is obtained by determining whether a distance norm $\Delta E = \|(x, y);(x_c, y_c)\|$ between the color of said object point (x, y) and the color of said reference color coordinate ($x_c$, $y_c$) exceeds a threshold $A_s$ with the first state ("0") of said two state digital color coordinate information ("0", "1") being then associated with said object point (x, y); whereas, if said distance norm $\Delta E$ is less than said threshold $A_s$, then the second state ("1") of said two state digital color coordinate information ("0", "1") is assigned to a pixel; and,
said visualization unit being further configured to display evaluated information defined by said two state digital color coordinate information ("0", "1") in said image of said area within said surgical region so as to distinguish the edge region of tumor tissue in the human brain from remaining tissue.

2. The system of claim 1, wherein said computer unit is configured to compute said two state digital color coordinate information ("0", "1") from a color spacing of said determined color coordinate to a characteristic reference color coordinate.

3. The system of claim 1, wherein, with respect to the light from said object point, said computer unit is configured to determine the coordinates (R, G, B) of the color coordinate in the RGB-color space; and, is further configured to compute the color coordinate information from a deviation of the quotient R/B from the quotient $R_c/B_c$ to the coordinate ($R_c$, $G_c$, $B_c$) of a characteristic reference color coordinate wherein said quotient R/B is determined with respect to the coordinates (R, G, B) of said color coordinate.

4. The system of claim 1, wherein said computer unit includes an input for inputting information as to a characteristic reference color coordinate.

5. The system of claim 1, wherein said detection unit includes a spectrometer for detecting the color coordinate of said light from said object point; and, said spectrometer is configured to spectrally disperse light.

6. The system of claim 1, further comprising:
an illumination unit configured to provide a time-sequential RGB illumination; and,
said detection unit including a light-sensitive flat electronic image sensor for detecting said color coordinate of the light as to said object point.

7. The system of claim 1, further comprising an illumination unit for providing illumination light in a wavelength range to make possible an excitation of a colorant to fluorescence in said surgical region.

8. The system of claim 7, wherein said wavelength range of said illumination light makes possible the fluorescence excitation of the colorant PPIX and/or sodium fluorescein and/or hypericin.

9. The system of claim 7, wherein said illumination unit generates light in a wavelength range of at least 380 nm to 680 nm; and, said system further comprises:
a viewing filter disposed upstream of said detection unit for passing said light from said object point before detection by said detection unit;
said illumination unit including optical elements for providing a resultant spectral transmission adapted to the fluorescence excitation spectrum of said colorant;
a total system including said optical elements of said illumination unit and said viewing filter; and,
said total system defining a resultant spectral transmission of more than 5% in only one wavelength region which extends maximally over 50 nm and has a resultant spectral transmission of less than 5% over the rest of the entire wavelength range.

10. The system of claim 7, wherein:
said illumination unit generates light in a wavelength range of at least 380 nm to 680 nm;
said system further comprising:
a viewing filter disposed upstream of said detection unit for passing said light from said object point before detection by said detection unit;
said illumination unit including optical elements for providing a resultant spectral transmission having a first pass range adapted to the fluorescence excitation spectrum of said colorant and a second pass range having wavelengths lying between the wavelengths of the fluorescence excitation spectrum and the wavelengths of the fluorescence spectrum;
said viewing filter having a spectral transmission which has a first pass range adapted to the fluorescence spectrum of said colorant and a second pass range which lies in the same wavelength range as said second range of said illumination unit;
a total system including said illumination unit and said viewing filter; and,
said total system defining a resultant spectral transmission of more than 5% in only one wavelength region which extends maximally over 50 nm and has a resultant spectral transmission of less than 5% over the rest of the entire wavelength range.

11. The system of claim 1, wherein said computer unit is configured to correlate the two state digital computed color coordinate information ("0", "1") with preoperatively obtained patient data for the coordinate correct visualization.

12. The system of claim 1, further comprising:
a main objective configured to pass light from an object point in said surgical region along a viewing beam path including a right viewing beam path; and,
a beam splitter configured to superpose said color coordinate information into said right viewing beam path.

13. A surgical microscope for viewing a surgical region, the surgical microscope comprising:
a main body;
a main objective mounted in said main body for passing light from an object point in said surgical region along a viewing beam path;
an optical decoupling device for coupling at least a portion of said light from said object point out of said viewing beam path;
a system for visualizing characteristic tissue in said surgical region to determine an edge region of tumor tissue in a human brain;
said system including:
a detection unit including at least one sensor and configured to detect light from an object point (x, y) in said surgical region;
a computer unit connected to said detection unit and having a computer processor;
a visualization unit having a display and being driven by said computer unit and configured to display unevaluated information defined by an image of an area within said surgical region;
said computer unit including a non-transitory computer readable storage medium having program code stored therein;
said computer processor being configured to run said program code;
said computer unit being configured to determine a color coordinate having a position in a color region as to said light from said object point (x, y);
said computer unit being further configured to compute, in dependence upon said position of the determined color coordinate in said color region, a two state digital color coordinate information ("0", "1") for controlling said visualization unit by comparing information as to said determined color coordinate to a characteristic reference color coordinate $(x_c, y_c)$ typical for said edge region of said tumor tissue in said color region in accordance with said program code wherein said two state digital color coordinate information ("0", "1") can have a first state ("0") or a second state ("1") and wherein said color coordinate information ("0", "1") is obtained by determining whether a distance norm $\Delta E = \|(x, y); (x_c, y_c)\|$ between the color of said object point (x, y) and the color of said reference color coordinate $(x_c, y_c)$ exceeds a threshold $A_s$ with the first state ("0") of said two state digital color coordinate information ("0", "1") being then associated with said object point (x, y); whereas, if said distance norm $\Delta E$ is less than said threshold $A_s$, then the second state ("1") of said two state digital color coordinate information ("0", "1") is assigned to a pixel; and,
said visualization unit being further configured to display evaluated information defined by said two state digital color coordinate information ("0", "1") in said image of said area within said surgical region so as to distinguish the edge region of tumor tissue in the human brain from remaining tissue.

14. A method for visualizing characteristic tissue in a surgical region to determine an edge region of tumor tissue in a human brain, the method comprising the steps of:
detecting light from an object point (x, y) in said surgical region with a detection unit including at least one sensor and configured to detect light from said object point (x, y);
providing a computer unit connected to said detection unit and having a computer processor;
providing a visualization unit having a display and being driven by said computer unit and configured to display unevaluated information defined by an image of an area within said surgical region;

wherein said computer unit includes a non-transitory computer readable storage medium having program code stored therein;

wherein said computer processor is configured to run said program code;

configuring said computer unit to determine a color coordinate having a position in a color region as to said light from said object point (x, y);

further configuring said computer unit to compute, in dependence upon said position of the determined color coordinate in said color region, a two state digital color coordinate information ("0", "1") for controlling said visualization unit by comparing information as to said determined color coordinate to a characteristic reference color coordinate ($x_c$, $y_c$) typical for said edge region of said tumor tissue in said color region in accordance with said program code wherein said two state digital color coordinate information ("0", "1") can have a first state ("0") or a second state ("1") and wherein said color coordinate information ("0", "1") is obtained by determining whether a distance norm $\Delta E = \|(x, y); (x_c, y_c)\|$ between the color of said object point (x, y) and the color of said reference color coordinate ($x_c$, $y_c$) exceeds a threshold $A_s$ with the first state ("0") of said two state digital color coordinate information ("0", "1") being then associated with said object point (x, y); whereas, if said distance norm $\Delta E$ is less than said threshold $A_s$, then the second state ("1") of said two state digital color coordinate information ("0", "1") is assigned to a pixel; and, further configuring said visualization unit to display evaluated information defined by said two state digital color coordinate information ("0", "1") in said image of said area within said surgical region so as to distinguish the edge region of tumor tissue in the human brain from remaining tissue.

15. A program code stored on a non-transitory computer-readable medium, the program code being for carrying out the following steps in a method for visualizing characteristic tissue in a surgical region to determine an edge region of tumor tissue in a human brain when these steps are carried out in a computer, namely, the steps of:

detecting light from an object point (x, y) in said surgical region with a detection unit including at least one sensor and configured to detect light from said object point (x, y);

providing a computer unit connected to said detection unit and having a computer processor;

providing a visualization unit having a display and being driven by said computer unit and configured to display unevaluated information defined by an image of an area within said surgical region;

wherein said computer unit includes a non-transitory computer readable storage medium having program code stored therein;

wherein said computer processor is configured to run said program code;

configuring said computer unit to determine a color coordinate having a position in a color region as to said light from said object point (x, y);

further configuring said computer unit to compute, in dependence upon said position of the determined color coordinate in said color region, a two state digital color coordinate information ("0", "1") for controlling said visualization unit by comparing information as to said determined color coordinate to a characteristic reference color coordinate ($x_c$, $y_c$) typical for said edge region of said tumor tissue in said color region in accordance with said program code wherein said two state digital color coordinate information ("0", "1") can have a first state ("0") or a second state ("1") and wherein said color coordinate information ("0", "1") is obtained by determining whether a distance norm $\Delta E = \|(x, y); (x_c, y_c)\|$ between the color of said object point (x, y) and the color of said reference color coordinate ($x_c$, $y_c$) exceeds a threshold $A_s$ with the first state ("0") of said two state digital color coordinate information ("0", "1") being then associated with said object point (x, y); whereas, if said distance norm $\Delta E$ is less than said threshold $A_s$, then the second state ("1") of said two state digital color coordinate information ("0", "1") is assigned to a pixel; and, further configuring said visualization unit to display evaluated information defined by said two state digital color coordinate information ("0", "1") in said image of said area within said surgical region so as to distinguish the edge region of tumor tissue in the human brain from remaining tissue.

16. The surgical microscope of claim 13, further comprising:

said viewing beam path including a right viewing beam path; and, a beam splitter being configured to superpose said color coordinate information into said right viewing beam path.

17. The method of claim 14, wherein said reference color coordinate is pregiven; and, for the control of a display information visualized via said visualization system, computing the color distance of the color coordinate, which is determined with respect to an object point, to the pregiven reference color coordinate.

18. The method of claim 14, further comprising the step of superposing the color coordinate information onto a viewing beam path via a beam splitter.

* * * * *

UNITED STATES PATENT AND TRADEMARK OFFICE
CERTIFICATE OF CORRECTION

| | | |
|---|---|---|
| PATENT NO. | : 9,727,962 B2 | Page 1 of 1 |
| APPLICATION NO. | : 13/946716 | |
| DATED | : August 8, 2017 | |
| INVENTOR(S) | : Hauger et al. | |

It is certified that error appears in the above-identified patent and that said Letters Patent is hereby corrected as shown below:

In the Claims

In Column 3:
Line 53: Table 1: insert -- Standard deviation: 0.03 (column x) 0.02 (column y) --.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*